United States Patent [19]

Watanabe et al.

[11] Patent Number: 4,897,420

[45] Date of Patent: Jan. 30, 1990

[54] BENZOQUINONE DERIVATIVES, THEIR PRODUCTION AND USE

[75] Inventors: Masazumi Watanabe, Kawanishi; Isuke Imada, Izumi, both of Japan

[73] Assignee: Takeda Chemical Industries, Ltd., Osaka, Japan

[21] Appl. No.: 280,153

[22] Filed: Dec. 5, 1988

Related U.S. Application Data

[62] Division of Ser. No. 848,115, Apr. 4, 1986, abandoned.

[30] Foreign Application Priority Data

Apr. 8, 1985 [JP] Japan ................................. 60-75081

[51] Int. Cl.[4] ..................... A61K 31/12; A61K 31/22; C07C 50/30; C07C 69/24
[52] U.S. Cl. ............................... 514/546; 260/396 R; 260/552; 260/307; 514/683; 514/691; 514/826; 560/130; 560/138; 560/140; 560/141; 560/231; 560/254; 560/255; 562/478; 562/508; 568/640; 568/643; 568/644; 568/651
[58] Field of Search ..................... 260/396 R; 514/546, 514/683, 691, 826

[56] References Cited

U.S. PATENT DOCUMENTS

| | | |
|---|---|---|
| 3,261,849 | 7/1966 | Wagner et al. ............... 260/396 R |
| 3,728,362 | 4/1973 | Morimoto et al. ............ 260/396 R |
| 3,728,363 | 4/1973 | Morimoto et al. ............ 260/396 R |
| 3,849,453 | 11/1974 | Morimoto et al. ............ 260/396 R |
| 4,139,545 | 2/1979 | Morimoto et al. ............ 260/396 R |
| 4,358,461 | 11/1982 | Maki et al. ........................ 514/683 |
| 4,436,753 | 3/1984 | Imada et al. ...................... 514/683 |
| 4,514,420 | 4/1985 | Imada et al. ...................... 514/689 |
| 4,559,177 | 12/1985 | Okutani et al. ................ 260/396 R |

FOREIGN PATENT DOCUMENTS

| | | |
|---|---|---|
| 21841 | 1/1981 | European Pat. Off. . |
| 31727 | 7/1981 | European Pat. Off. . |
| 58057 | 8/1982 | European Pat. Off. . |
| 1493980 | 7/1969 | Fed. Rep. of Germany . |
| 2055097 | 2/1981 | United Kingdom ............ 260/396 R |

OTHER PUBLICATIONS

Okamoto et al., Chem. Pharm. Bull., 36, (1) pp. 178-189 (1988).

*Primary Examiner*—Vivian Garner
*Attorney, Agent, or Firm*—Wenderoth, Lind & Ponack

[57] ABSTRACT

Compounds of the formula:

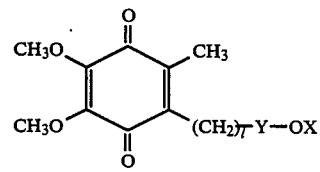

wherein $l$ is an integer of 0 to 18, X is hydrogen, an alkyl having 1 to 4 carbon atoms or a carboxylic acyl having 2 to 4 carbon atoms and Y is a phenylene, a cycloalkylene having 3 to 7 carbon atoms or a group of the formula:

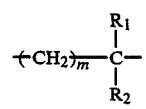

in which m is an integer of 0 to 3, and $R_1$ and $R_2$ each is an alkyl having 1 to 4 carbon atoms, are novel compounds, possess circulatory disturbance-improving activity and inhibitory activity of the generation and release of SRS-A, and used for prophylactic or therapy of ischemic diseases such as cerebral apoplexy or allergic diseases.

9 Claims, No Drawings

BENZOQUINONE DERIVATIVES, THEIR PRODUCTION AND USE

This application is a division of application Ser. No. 848,115 filed Apr. 4, 1986, now abandoned.

This invention relates to novel benzoquinone derivatives useful in the medicinal field, for example as circulatory disturbance-improving agents or antiallergic agents.

Various benzoquinone derivatives are so far known to have circulatory disturbance-improving activity and antiallergic activity (Japanese Patent Publications Kokai No. 128932/1976, No. 97223/1981 and No. 150014/1981).

However, these known compounds are metabolized rapidly and are short in duration of their action.

It is an object of the invention to provide novel benzoquinone derivatives which are at least comparable in pharmacological activity to the known benzoquinone derivatives and at the same time are long-acting.

This invention relates to:

1. Benzoquinone derivatives of the general formula:

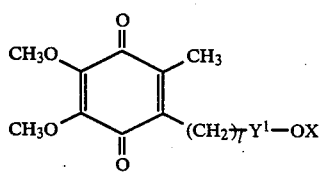

wherein $l$ is an integer of 0 to 18, X is hydrogen, an alkyl having 1 to 4 carbon atoms or a carboxylic acyl having 2 to 4 carbon atoms and Y is a phenylene, a cycloalkylene or a group of the formula:

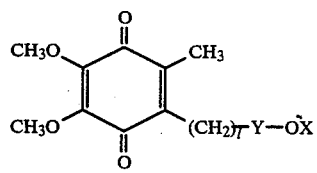

in which m is an integer of 0 to 3, and $R_1$ and $R_2$ each is an alkyl having 1 to 4 carbon atoms.

2. A pharmaceutical composition suitable for the treatment of a mammal suffering from allergic disease due to SRS-A or from ischemic disease, which comprises, as an active ingredient, an effective amount of a compound of the formula (I).

3. A method for producing a compound of the formula:

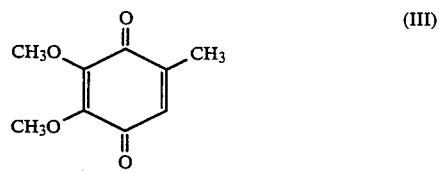

wherein $l$ and X have the meanings given above and $Y^1$ is a cycloalkylene having 3 to 7 carbon atoms or a group of the formula:

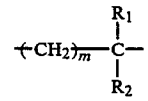

wherein each symbol has the meaning given above, which comprises oxidizing a compound of the formula:

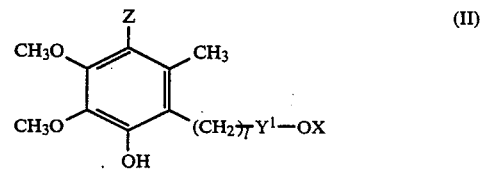

wherein Z is hydrogen or hydroxyl and the other symbols have the meanings given above.

4. A method for producing a compound of the formula:

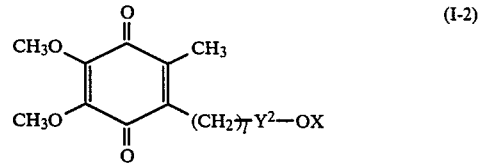

wherein $Y^2$ is a phenylene or a cycloalkylene having 3 to 7 carbon atoms and the other symbols have the meanings given above, which comprises reacting a compound of the formula:

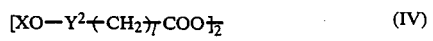

with a peroxide of the formula:

$$[XO-Y^2+CH_2)_{\overline{l}}COO]_{\overline{2}} \quad (IV)$$

wherein each symbol has the meaning given above.

In the above general formulas (I) to (IV), the alkyl having 1 to 4 carbon atoms represented by X includes methyl, ethyl, i-propyl, n-butyl, i-butyl, etc.; the carboxylic acyl having 2 to 4 carbon atoms represented by X includes acetyl, n-propionyl, n-butyryl, etc. The cycloalkylene having 3 to 7 carbon atoms represented by Y, $Y^1$ and $Y^2$ includes cyclopropylene, cyclobutylene, cyclopentylene, cyclohexylene, etc.; a preferred example is cyclopentylene or cyclohexylene and the most preferred one is 1,4-cyclohexylene. When Y is phenylene, a preferred example is 1,4-phenylene.

The alkyl having 1 to 4 carbon atoms represented by $R_1$ or $R_2$ includes methyl, ethyl, i-propyl, n-butyl, i-butyl, etc.

When the formula —Y—OX represents

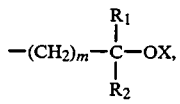

the sum of l and m is preferably 7 to 11, when Y is a phenylene or a cycloalkylene, the integer l is preferably 4 to 8, and most preferably 6.

The compounds of general formula (I) show electron-transporting activity in the mitochondrial succinate oxidase system and have cellular energy metabolism activating activity. They also inhibit NADPH- and $Fe^{++}$-dependent lipid peroxide formation in the liver and brain.

The compound (I) has less toxicity. The compound (I) shows circulatory disturbance-improving activity in mammals (e.g. human being, mouse, rat, rabbit, dog and monkey), and is used for prophylactic or therapy of ischemic diseases such as cerebral apoplexy (e.g. cerebral infarction, cerebral hemorrhage, etc.) and cardiac insufficiency (cardiac infraction, angina pectoris, etc.).

The compound (I) also inhibits the generation and release of SRS-A in mammals mentioned above, and it is used for prophylactic, or therapy of various allergic diseases due to SRS-A (e.g. bronchial asthma, allergic rhinitis, urticaria).

The compound (I) has protocellagen proline hydroxylase-inhibiting activity and collagen biosynthesis-inhibiting activity and can be used as an antifibrotic drug for the therapy of organ fibrosis in mammals mentioned above.

Furthermore, as shown in a test in which they were incubated with rat liver slices or orally administered to rats, followed by investigation of metabolites in the liver tissue, the compounds (I) are hardly liable to side chain oxidation by $\beta$-oxidation and, when administered to living bodies, they are long-acting.

The compounds (I) are orally or parenterally administered either as they are or in admixture with an appropriate carrier or vehicle, for example in the form of powders, granules, tablets or injections.

Pharmaceutical compositions containing compounds (I) are produced by any method per se known for the production of powders, capsules, tablets, granules, injections, etc.

The dose of compounds (I) may vary, and can be selected suitably, depending, for example, on the kind of the objective compounds, symptoms, etc. For improving circulatory disturbances, they are administered in a dose of 0.2 to 5 mg/kg, preferably 0.5 to 1.5 mg/kg.

The compound (I-1) can be prepared by oxidizing a compound (II). The means of oxidation may be any means which can convert phenols to quinones. Thus, the oxidizing agent may be, for example hydrogen peroxide, peracetic acid, performic acid, perbenzoic acid, potassium permanganate, potassium dichromate, chromic anhydride, potassium nitrosodisulfonate, ferric chloride, silver oxide, manganese dioxide, or catalytic oxygen oxidation with salcomin (bissalicylideneethylenediiminocobalt) as a catalyst. The reaction is carried out in an appropriate solvent. Examples of the solvent are dilute aqueous alkali solutions, acetone, methanol, ethanol, ether, tetrahydrofuran, dioxane, dimethylformamide and acetic acid. The reaction temperature and time vary depending on the kind of oxidizing agent employed. Generally and preferably, however, the reaction is carried out at a temperature of about 0° C. to 25° C. for a period of 0.5 to 5 hours. The use of an appropriate buffer, such as a phosphate buffer, gives favorable results.

The compounds (I-2) can be obtained by reacting a compound (III) with a peroxide of the formula (IV).

The reaction between compound (III) and peroxide (IV) is preferably carried out in an appropriate inert solvent, such as hexane, ligroin, toluene, xylene, acetic acid or propionic acid. A preferred reaction temperature is about 80° C. to 100° C. and a preferred reaction period is 0.5 to 5 hours.

Said reaction may also be conducted under conditions such that the peroxide is formed in the reaction system. For instance, the compound (III) is reacted with a carboxylic acid of the formula:

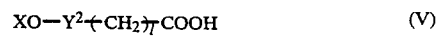

wherein each symbol is the meaning given above, or with an acid anhydride thereof in the presence of lead tetraacetate or the like to give a compound (I-2).

The reaction is conducted essentially in the same manner as the above reaction between compound (III) and peroxide (IV).

When X is a hydrogen atom, the compounds (I-2) can be converted, by alkylation or acylation, to the corresponding compounds in which X is alkyl or carboxylic acyl. The alkylation is effected by using an alkyl halide (e.g. methyl iodide, ethyl bromide) or an alkyl sulfate (e.g. dimethyl sulfate, diethyl sulfate) in the presence of a base catalyst (e.g. lithium hydride, butyllithium). The acylation is conducted by using a carboxy-modified reactive derivative of a fatty acid (e.g. carboxylic acid anhydride, carboxylic acid halide, carboxylic acid metal salt) in the presence of an acid or base catalyst.

When the thus-obtained compounds (I-2) have an acylated hydroxy group, they can be converted, by hydrolysis using a per se known means, to the corresponding compounds (I-2) in which X is a hydrogen atom.

The compound (II) shown above is novel and can be prepared by the following procedures.

(i)

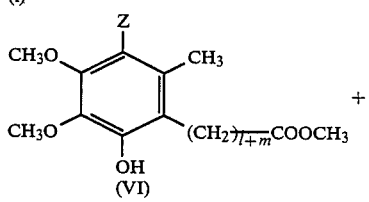

(ii)

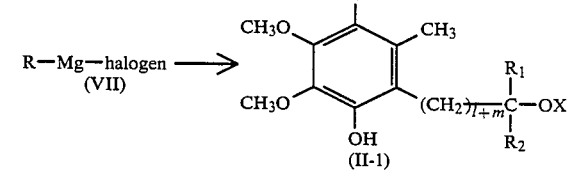

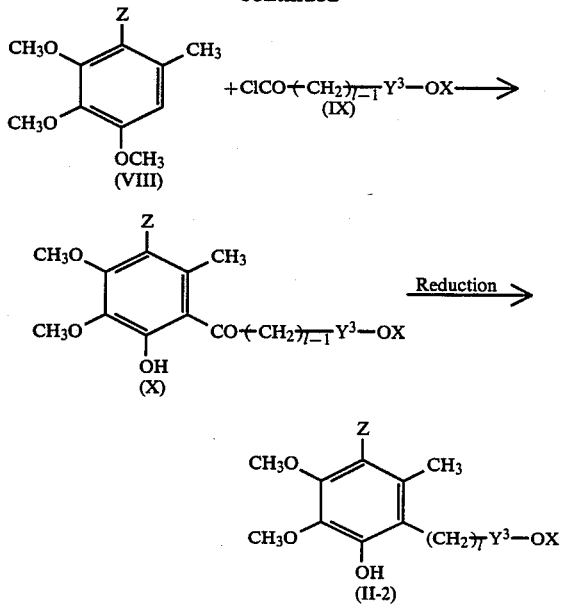

In the above formulas, $Y^3$ is a cycloalkylene having 3 to 7 carbon atoms (e.g. cyclopropylene, cyclobutylene, cyclopentylene, cyclohexylene, etc.), R is alkyl having 1 to 4 carbon atoms (e.g. methyl, ethyl, n-propyl, i-propyl, n-butyl, etc.), and the other symbols have the meaning given above.

The compound (II-1) can be prepared by reacting a compound (VI) with a Grignard reagent (VII). The Grignard reagent (VII) can be prepared by reacting an alkyl halide such as methyl iodide, ethyl iodide, ethyl bromide, etc. with magnesium metal in an organic solvent such as an ether (e.g. diethylether, tetrahydrofuran, dioxan). The reaction is desirably carried out at a temperature ranging 0° C. to 70° C. The compound (II-1) can be prepared by adding a compound (VI) to the resulting Grignard reagent (VII), followed by diluting with water and then by acidifying the reaction mixture.

The compound (II-2) can be prepared by reacting a compound (VIII) with a compound (IX) to give a compound (X), followed by reducing the compound (X).

The reaction of a compound (VIII) with a compound (IX) is carried out preferably in the presence of a catalyst. As the catalyst, any catalysts employed in the Friedel-Crafts Reaction, for example, sulfonic acid, phosphoric acid, poly phosphoric acid, and Lewis acids such as aluminum chloride are employed. While this reaction proceeds in the absence of a solvent, it is usually conducted in the presence of an inert solvent such as nitrobenzene, carbon disulfide, tetrachloroethane. The reaction temperature is advantageously about 50° C.–150° C.

The procedure of reducing a compound (X) may be any procedure by which the carbonyl of the compounds (X) may be converted to a methylene. As such procedures, there may be mentioned Clemmensen reduction, Wolff-Kishner reduction, a method comprising converting the starting compound to the dithioacetate and reducing the latter through desulphurization, and catalytic reduction. Generally, this reaction is advantageously conducted in the presence of a suitable solvent. The solvent may be any solvent that does not interfere with the reaction, being exemplified by ether, methanol, ethanol, benzene, toluene, xylene, ethylene glycol, triethylene glycol, acetic acid and so on. The aforementioned reduction reactions may each be easily carried out in the routine manner.

The peroxide represented by the formula (IV) is novel, and can be prepared by reacting an acid halide or an acid anhydride of a carboxylic acid of the formula (V) with a peroxide such as hydrogen peroxide, metal salt thereof or lead tetraacetate.

The compounds (V), (VI) and (IX) include novel compounds as well as known compounds within their respective scopes. Such novel compounds can be produced by the same processes as known for the known compounds or by modifications of such processes.

EXAMPLE 1

Potassium nitrosodisulfonate (12 g) and sodium acetate (12 g) are suspended in methanol-water (5:2, 210 ml), and 11-(2-hydroxy-3,4-dimethoxy-6-methylpheyl)-2-methylundecan-2-ol (2.4 g) is added thereto. The mixture is stirred at 50° C. for 14 hours and then diluted with water (100 ml). The methanol is distilled off. The aqueous soliution is extracted with ethyl acetate (200 ml), and the extract is washed with water, dried and concentrated under reduced pressure. The residue is subjected to silica gel column chromatography to give 1.7 g of 6-(10-hydroxy-10-methylundecyl)-2,3-dimethoxy-5-methyl-1,4-benzoquinone as an orange oil.

Nuclear magnetic resonance spectrum (in deuteriochloroform, $\delta$ value): 1.18 ($CH_3$, singlet), 1.32 ($CH_2$, singlet), 1.98 ($CH_3$ on the ring, singlet), 2.17 (OH, singlet), 1.38–1.60 ($CH_2$ on the ring, multiplet), 3.95 ($OCH_3$, singlet).

Elemental analysis for $C_{21}H_{34}O_5$: Calcd. C, 68.82; H, 9.35. Found C, 68.63; H, 9.27.

EXAMPLE 2

Bis[6-(4-methoxyphenyl)hexanoyl]peroxide (3.6 g) is added portionwise to a solution of 2,3-dimethoxy-5-methyl-1,4-benzoquinone (1.48 g) in acetic acid (30 ml) with stirring at 95° C. The mixture is heated for an hour and the acetic acid is distilled off under reduced pressure. The residue is diluted with water and extracted with ether. The ether extract is washed with water, dried and concentrated under reduced pressure. The residue is subjected to silica gel column chromatography to give 0.46 g of 2,3-dimethoxy-6-[5-(4-methoxyphenyl)pentyl]-5-methyl-1,4-benzoquinone as an orange oil.

Nuclear magnetic resonance spectrum (in deuteriochloroform, $\delta$ value): 1.20–1.80 ($CH_2$, broad), 1.98 ($CH_3$ on the ring, singlet), 2.27–2.67 ($CH_2$ on the ring, multiplet), 3.77 ($OCH_3$, singlet), 3.97 ($OCH_3$, singlet), 6.70 (aromatic H, doublet), 7.00 (aromatic H, doublet).

EXAMPLE 3

Bis[7-(4-acetoxyphenyl)heptanoyl]peroxide (8.96 g) is reacted with 2,3-dimethoxy-5-methyl-1,4-benzoquinone (3.1 g) in the same manner as Example 2, followed by purification by silica gel column chromatography to give 2.1 g of 6-[6-(4-acetoxyphenyl)hexyl]-2,3-dimethoxy-5-methyl-1,4-benzoquinone.

Infrared adsorption spectrum $\nu_{max}^{film}$ cm$^{-1}$: 1760 ($OCOCH_3$), 1640, 1610 (quinone).

Nuclear magnetic resonance spectrum (in deuteriochloroform, $\delta$ value): 1.40 ($CH_2$, broad), 2.00 ($CH_3$ on the ring, singlet), 2.29 (COCH$_3$, singlet), 2.53 (CH$_2$ on the ring, multiplet), 3.97 (OCH$_3$, singlet).

EXAMPLE 4

6-[6-(4-Acetoxyphenyl)hexyl]-2,3-dimethoxy-5-methyl-1,4-benzoquinone (2.1 g) is dissolved in a mixture of concentrated hydrochloric acid (0.3 ml) and methanol (55 ml), and the solution is allowed to stand at room temperature for 4 hours. The methanol is distilled off under reduced pressure, and the residue is diluted with water and extracted with ethyl acetate (200 ml). The extract is washed with water and dried. The solvent is then distilled off under reduced pressure and the residue is purified by silica gel column chromatography. The fractions containing the desired product are recrystallized from ether-hexane to give 830 mg of 6-[6-(4-hydroxyphenyl)hexyl]-2,3-dimethoxy-5-methyl-1,4-benzoquinone, m.p. 87°–88° C.

Nuclear magnetic resonance spectrum (in deuteriochloroform, δ value): 1.80–1.00 (CH$_2$, multiplet), 2.17 (CH$_3$ on the ring, singlet), 2.17–2.67 (CH$_2$ on the ring, multiplet), 3.98 (OCH$_3$, singlet), 5.1 (OH, singlet), 6.63 (aromatic H, doublet), 6.93 (aromatic H, doublet).

Elemental analysis for C$_{21}$H$_{26}$O$_5$: Calcd. C, 70.37; H, 7.31 Found C, 70.09; H, 7.38.

EXAMPLE 5

Bis[trans-6-(4-acetoxycyclohexyl)hexanoyl]peroxide (4.8 g) is reacted with 2,3-dimethoxy-5-methyl-1,4-benzoquinone (1.7 g) in the same manner as in Example 2. Crystallization from petroleum ether gives 814 mg of trans-6-[5-(4-acetoxycyclohexyl)pentyl]-2,3-dimethoxy-5-methyl-1,4-benzoquinone as orange crystals, m.p. 33°–34° C.

Elemental analysis for C$_{22}$H$_{32}$O$_6$: Calcd. C, 67.32; H, 8.22 Found C, 67.59; H, 8.17.

EXAMPLE 6 trans-6-[5-(4-Acetoxycyclohexyl)pentyl]-2,3-dimethoxy-5-methyl-1,4-benzoquinone (0.415 g) is dissolved in hydrochloric acid-methanol (1.180, 10 ml), and the mixture is stirred at room temperature for 24 hours. The solvent is distilled off under reduced pressure, and the residue is dissolved in ether, washed with aqueous sodium hydrogen carbonate and then with water and dried. The ether is distilled off and the residue is subjected to silica gel column chromatography. Recrystallization of the desired fractions from ether-hexane gives trans-6-[5-(4-hydroxycyclohexyl)pentyl]-2,3-dimethoxy-5-methyl-1,4-benzoquinone as orange needles, m.p. 64°–65° C.

Nuclear magnetic resonance spectrum (in deuteriochloroform, δ value): 0.97–1.90 (CH$_2$, multiplet), 2.00 (CH$_3$ on the ring, singlet), 2.43 (CH$_2$ on the ring, triplet), 3.53 (>CHOH, broad), 3.98 (OCH$_3$, singlet).

Elemental analysis for C$_{20}$H$_{30}$O$_5$: Calcd. C, 68.54; H, 8.63 Found C, 68.78; H, 8.33.

EXAMPLE 7

A cis-trans mixture of bis[6-(4-acetoxycyclohexyl)hexanoyl]peroxide (500 mg) is reacted with 2,3-dimethoxy-5-methyl-1,4-benzoquinone (182 mg) in the same manner as Example 2. Purification of the crude product by silica gel column chromatography gives 80 mg of cis-trans mixture of 6-[5-(4-acetoxycyclohexyl)pentyl]-2,3-dimethoxy-5-methyl-1,4-benzoquinone.

Nuclear magnetic resonance spectrum (in deuteriochloroform, δ value): 1.28 (CH$_2$, broad), 2.00 (CH$_3$ on the ring, singlet), 2.02 (OCOCH$_3$, singlet), 2.43 (CH$_2$ on the ring, triplet), 3.97(OCH$_3$, singlet), 4.92 (>CHO-CO—, broad).

EXAMPLE 8

A cis-trans mixture of 6-[5-(4-acetoxycyclohexyl)pentyl]-2,3-dimethoxy-5-methyl-1,4-benzoquinone (1.3 g) is subjected to hydrolysis in the same manner as Example 6, followed by separation by silica gel column chromatography. The first ethyl acetate-carbon tetrachloride (1:9) eluate fraction is recrystallized from ether-hexane to give cis-6-[5-(4-hydroxycyclohexyl)pentyl]-2,3-dimethoxy-5-methyl-1,4-benzoquinone (488 mg) as orange needles, m.p. 49°–51° C.

Nuclear magnetic resonance spectrum (in deuteriochloroform, δ value): 1.13–1.70 (CH$_2$, broad), 2.02 (CH$_3$ on the ring, singlet), 2.47 (CH$_2$ on the ring, triplet), 3.98 (OCH$_3$, >CHOH, singlet).

Recrystallization of the second fraction fraom ether-hexane gives trans-6-[5-(4-hydroxycyclohexyl)pentyl]-2,3-dimethoxy-5-methyl-1,4-benzoquinone (216 mg) as orange needles, m.p. 64°–65° C.

EXAMPLE 9

Bis[trans-7-(4-acetoxycyclohexyl)heptanoyl]peroxide (5.9 g) is reacted with 2,3-dimethoxy-5-methyl-1,4-benzoquinone (1.82 g) in the same manner as Example 2. Thereafter, the crude product is purified by silica gel column chromatography to give trans-6-[6-(4-acetoxycyclohexyl)hexyL]-2,3-dimethoxy-5-methyl-1,4-benzoquinone (2.2 g). This product is hydrolyzed in the same manner as Example 6 and subjected to silica gel column chromatography. The desired fractions are recrystallized from ether-petroleum ether to give trans-6-[6-(4-hydroxycyclohexyl)hexyl]-2,3-dimethoxy-5-methyl-1,4-benzoquinone (0.9 g) as orange needles, m.p. 69°–71° C.

Nuclear magnetic resonance spectrum (in deuteriochloroform, δ value): 1.00–2.10 (CH$_2$, multiplet), 2.00 (CH$_3$ on the ring, singlet), ;b 2.42 (CH$_2$ on the ring, triplet), 3.47 (>CHOH, broad), 3.97 (OCH$_3$, singlet).

Elemental analysis for C$_{21}$H$_{32}$O$_5$: Calcd. C, 69.20; H, 8.85 Found C, 69.26; H, 8.66.

EXAMPLE 10

Bis[cis-7-(4-acetoxycyclohexyl)heptanoyl]peroxide (26.5 g) is reacted with 2,3-dimethoxy-5-methyl-1,4-benzoquinone (4.95 g) in the same manner as Example 2. Thereafter, the crude product is purified by silica gel column chromatography to give cis-6-[6-(4-acetoxycyclohexyl)hexyl]-2,3-dimethoxy-5-methyl-1,4-benzoquinone (5.95 g). This product is hydrolyzed in the same manner as Example 6 and then subjected to silica gel column chromatography. The desired fractions are recrystallized from ether-hexane to give cis-6-[6-(4-hydroxycyclohexyl)hexyl]-2,3-dimethoxy-5-methyl-1,4-benzoquinone (1.73 g) as orange needles, m.p. 33.5°–35.5° C.

Elemental analysis for C$_{21}$H$_{32}$O$_5$: Calcd. C, 69.20; H, 8.85 Found C, 69.32; H, 8.56.

REFERENCE EXAMPLE 1

A solution of methyl iodide (4.9 g) in ether (17.3 ml) is added dropwise to a suspension of magnesium (0.92 g) in ether (6 ml). The suspension is warmed at 40° C. for 40 minutes, and tetrahydrofuran (50 ml) is added thereto, followed by addition of a solution of methyl 10-(2-hydroxy-3,4-dimethoxy-6-methylphenyl) decanoate (4.99 g) in tetrahydrofuran (50 ml) over 1.5 hours. The mixture is stirred at 40° C. for 30 minutes, and saturated aqueous ammonium chloride solution is added, followed by extraction with ether (300 ml). The extract is washed with water, dried and concentrated. The residue is isolated and purified by silica gel column chromatography using chloroform to give 11-(2-hydroxy-3,4-dimethoxy-6-methylphenyl)-2-methylundecan-2-ol (2.375 g, 48%).

Nuclear magnetic resonance spectrum (in deuteriochloroform, δ value): 1.18 ($CH_3$, singlet), 1.32 ($CH_2$, singlet), 2.17 ($CH_3$ on the ring, singlet), 1.40–1.64 ($CH_2$ on the ring, multiplet), 3.80, 3.83 ($OCH_3$, singlet), 6.02 (OH, singlet), 6.17 (H on the ring, singlet).

REFERENCE EXAMPLE 2

6-(4-Methoxyphenyl)hexanoic acid (3.7 g) is dissolved in thionyl chloride (5 ml) and the solution is stirred at room temperature overnight. The excess thionyl chloride is distilled off under reduced pressure and the residue is dissolved in petroleum ether (30 ml). Ice water (15 ml) is added to the solution and sodium peroxide (3 g) is added portionwise with ice-cooling and stirring. The mixture is extracted with chloroform and the extract is washed with water and dried. The solvent is then distilled off to give bis[6-(4-methoxyphenyl)hexanoyl]peroxide.

REFERENCE EXAMPLE 3

7-(4-Acetoxyphenyl)heptanoic acid (10 g) is dissolved in thionyl chloride (14 ml) and the solution is heated at 70° C. for 1.5 hours. The excess thionyl chloride is distilled off under reduced pressure to give a crude acid chloride.

Infrared absorption spectrum $\nu_{max}^{CHCl_3}cm^{-1}$: 1790(COCl), 755 ($OCOCH_3$).

The above crude acid chloride (11.2 g) is dissolved in ether (75 ml), and 30% aqueous hydrogen peroxide (3.5 ml) is added dropwise thereto at 0° to 5° C. Thereafter, pyridine (7.2 ml) is added, and the mixture is stirred at room temperature for an hour. The ether layer is separated, washed with water and dried, and the ether is distilled off under reduced pressure to give bis[7-(4-acetoxyphenyl)heptanoyl]peroxide (8.9 g, 90%) as a white solid.

Infrared absorption spectrum $\nu_{max}^{CHCl_3}cm^{-1}$:

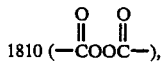

1810 (—COOC—), 1750 ($OCOCH_3$).

REFERENCE EXAMPLE 4 trans-6-(4-Hydroxycyclohexyl)hexanoic acid (5 g) is dissolved in acetic anhydride (25 ml), and p-toluenesulfonic acid (10 mg) is added to the solution. The mixture is stirred at 60° to 70° C. for an hour. The excess acetic anhydride is distilled off under reduced pressure and, after addition of water, the mixture is stirred at room temperature for 24 hours and then at 50° to 60° C. for further 5 hours and poured into ice-water. The resulting crystalline precipitate is recrystallized from ethanol-water to give 4.93 g (82%) of trans-6-(4-acetoxycyclohexyl)hexanoic acid as colorless needles, m.p. 82°–86° C.

Nuclear magnetic resonance spectrum (in deuteriochloroform, δ value): 0.9–1.9 ($CH_2$, multiplet), 2.00 ($COCH_3$, singlet), 2.32 ($CH_2COO$, triplet), 4.60 (>CH—OCO, broad), 10.12 (COOH, broad).

Elemental analysis for $C_{14}H_{24}O_4$, Calcd. C, 65.59; H, 9.44 Found C, 65.76; H, 9.45.

trans-6-(4-Acetoxycyclohexyl)hexanoic acid (4.8 g) is dissolved in thionyl chloride (5 ml), and the solution is allowed to stand at room temperature for 3 days. The excess thionyl chloride is distilled off under reduced pressure to give a crude acid chloride. This product is dissolved in petroleum ether (40 ml), and ice-water (20 ml) is added. Thereafter, sodium peroxide (3 g) is added portionwise with ice-cooling and stirring. The mixture is extracted with chloroform and the extract is washed with saturated aqueous sodium chloride and dried over calcium chloride. The solvent is then distilled off under reduced pressure to give bis[trans-6-(4-acetoxycyclohexyl)hexanoyl]peroxide.

Infrared absorption spectrum $\nu_{max}^{Film}cm^{-1}$: 1810,

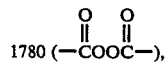

1780 (—COOC—), 1740 ($OCOCH_3$).

REFERENCE EXAMPLE 5

6-(4-Hydroxyphenyl)hexanoic acid (2 g) is subjected to catalytic reduction in the presence of 5% rhodium-carbon (500 mg) in ethanol (100 ml) at an initial hydrogen pressure of 10.1 kg/cm². The catalyst is filtered off and the filtrate is concentrated under reduced pressure and subjected to silica gel column chromatography. Elution is carried out with 4% ethanol-chloroform to give three fractions. The first fraction is recrystallized from ether-ligroin to give 392 mg of cis-6-(4-hydroxycyclohexyl)hexanoic acid, m.p. 83°–85° C.

Nuclear magnetic resonance spectrum (in dimethyl sulfoxide-d₆, δ value): 1.25 ($CH_2$, broad), 2.18 ($CH_2COO$, triplet), 3.77 (>CHOH, broad).

Elemental analysis for $C_{12}H_{22}O_3$: Calcd. C, 67.25; H, 10.35 Found C, 67.47; H, 10.53.

The third fraction is recrystallized from ethanol-water to give 276 mg of trans-6-(4-hydroxycyclohexyl)hexanoic acid as colorless needles, m.p. 120°–127° C.

Nuclear magnetic resonance spectrum (in dimethyl sulfoxide-d₆, δ value): 0.9–1.8 ($CH_2$, multiplet), 2.18 ($CH_2COO$, triplet), 3.33 (>CHOH).

Elemental analysis for $C_{12}H_{22}O_3$: Calcd. C, 67.25; H, 10.35, Found C, 67.48; H, 10.64.

From the second fraction, there is obtained 922 mg of a cis-trans mixture of 6-(4-hydroxycyclohexyl)hexanoic acid.

REFERENCE EXAMPLE 6

7-(4-Hydroxyphenyl)heptanoic acid (20 g) is subjected to similar catalytic reduction as Reference Example 5 in 80% ethanol. Ether is added to the crude product to give crystals. Recrystallization from ethanol-water and then from i-propanol-ether give trans-7-(4-hydroxycyclohexyl)heptanoic acid (7 g) as colorless needles, m.p. 123°–128° C.

Ligroin is added to the ether-soluble fraction in the above procedure to give crystals. Recrystallization from ether-petroleum ether gives 8.6 g of cis-7-(4-hydroxycyclohexyl)heptanoic acid as colorless needless, m.p. 75°–79° C.

Elemental analysis for $C_{13}H_{24}O_3$: Calcd. C, 68.38; H, 10.59, Found C, 68.56; H, 10.36.

REFERENCE EXAMPLE 7 trans-7-(4-Hydroxycyclohexyl)heptanoic acid (6.5 g) and p-toluenesulfonic acid (15 mg) are stirred in acetic anhydride (32.5 ml) at 60°–70° C. for 1.5 hours. The excess acetic anhydride is distilled off under reduced pressure, followed by addition of water (90 ml), and the mixture is stirred for 3 days. The resulting crystalline precipitate is collected by filtration and recrystallized from ethyl acetate-hexane to give 6.5 g of trans-7-(4-acetoxycyclohexyl)heptanoic acid as colorless needless, m.p. 66°–68° C.

Nuclear magnetic resonance spectrum (in deuteriochloroform, δ value): 0.82–2.13 (CH$_2$, multiplet), 2.03 (COCH$_3$, singlet), 2.35 (CH$_2$COO, triplet), 4.65 (>CH—OH, broad), 8.13 (COOH, broad), Infrared absorption spectrum $\nu_{max}^{KBr}$ cm$^{-1}$: 1730(OCOCH$_3$), 1705(COOH), Elemental analysis for C$_{15}$H$_{26}$O$_4$: Calcd. C, 66.63; H, 9.69, Found C, 66.81; H, 9.83.

Thionyl chloride (6 ml) is added to trans-7-(4-acetoxycyclohexyl)heptanoic acid (6 g), and the mixture is stirred at room temperature for 2 hours and then at 60° C. for an hour. The excess thionyl chloride is distilled off under reduced pressure. The thus-obtained crude acid chloride is dissolved in ether (39 ml), and aqueous hydrogen peroxide (1.87 g) is added thereto with ice-cooling and stirring, followed by dropwise addition of pyridine (2.09 g) over 15 minutes. The mixture is stirred with ice-cooling for 15 minutes and at room temperature for 1.5 hours and then extracted with ether. The extract is washed with 3N hydrochloric acid (100 ml), water and further with 5% aqueous solution of sodium hydrogen carbonate and dried. The solvent is then distilled off under reduced pressure to give 5.9 g of bis[-trans-7-(4-acetoxycyclohexyl)heptanoyl]peroxide. as white crystals.

Infrared absorption spectrum $\nu_{max}^{Kbr}$ cm$^{-1}$: 1810, 1780 (—COOC—), 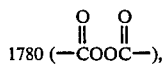
1730 (OCOCH$_3$).

We claim:

1. A compound of the formula

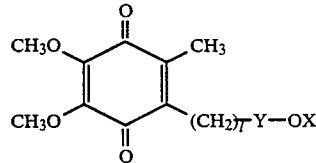

wherein l is an integer of 0 to 18, X is hydrogen, an alkyl having 1 to 4 carbon atoms or a carboxylic acyl having 2 to 4 carbon atoms and Y is a phenylene or a cycloalkylene having 3 to 7 carbon atoms.

2. A compound as claimed in claim 1, wherein Y is cyclohexylene.

3. A compound as claimed in claim 2, wherein l is an integer of 4 to 8.

4. A compound as claimed in claim 1, wherein X is hydrogen.

5. A compound as claimed in claim 1, wherein the compound is 6-[6-(4-hydroxycyclohexyl)hexyl]-2,3-dimethoxy-5-methyl-1,4-benzoquinone.

6. A compound as claimed in claim 1, wherein Y is phenylene.

7. A compound as claimed in claim 6, wherein l is an integer of 4 to 8.

8. A compound as claimed in claim 1, wherein Y is cycloalkylene having 3 to 7 carbon atoms.

9. A pharmaceutical composition for the treatment of a mammal suffering from allergic disease due to SRS-A or from ischemic disease, which comprises, as an active ingredient, an effective amount of a compound of the formula

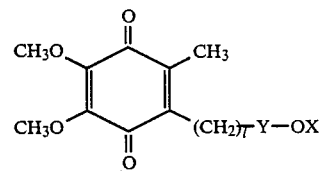

wherein l is an integer of 0 to 18, X is hydrogen, an alkyl having 1 to 4 carbon atoms or a carboxylic acyl having 2 to 4 carbon atoms and Y is a phenylene or a cycloalkylene having 3 to 7 carbon atoms and a pharmaceutically acceptable carrier therefor.

* * * * *